United States Patent [19]

Farahany

[11] Patent Number: 4,850,349
[45] Date of Patent: Jul. 25, 1989

[54] ENDOTRACHEAL TUBE SEALING CUFF SYSTEM

[76] Inventor: Amir H. Farahany, 1900 Randolph Rd., Ste. 400, Charlotte, N.C. 28207

[21] Appl. No.: 128,636

[22] Filed: Dec. 4, 1987

[51] Int. Cl.$^4$ ..................... A61M 16/00; A61M 25/00
[52] U.S. Cl. ........................... 128/207.15; 128/207.14; 128/207.16; 604/96; 604/97
[58] Field of Search .................. 128/202.15, 207.15, 128/207.16, 207.14, 204.21, 204.25, 203.12, 911, 912, 205.24; 137/505, 505.17, 496; 604/96, 97

[56] References Cited

U.S. PATENT DOCUMENTS

| | | | |
|---|---|---|---|
| 4,090,518 | 5/1978 | Elam | 128/207.15 |
| 4,119,101 | 10/1978 | Igich | 128/202.16 |
| 4,501,273 | 2/1985 | McGinnis | 128/207.15 |

FOREIGN PATENT DOCUMENTS

| | | | |
|---|---|---|---|
| 0143618 | 6/1985 | European Pat. Off. | 128/207.15 |
| 3435900 | 4/1986 | Fed. Rep. of Germany | 128/207.15 |

Primary Examiner—Edgar S. Burr
Assistant Examiner—Kimberly L. Asher
Attorney, Agent, or Firm—Pearne, Gordon, McCoy & Granger

[57] ABSTRACT

An inflation control system for an endotracheal tube cuff is disclosed. The control includes a housing defining a passage connected at one end to a respirator and at the other end to an endotracheal tube. The housing also defines a diaphragm chamber divided into two portions by a flexible diaphragm. One chamber portion is connected to the passage and the other to an inflatable cuff on the endotracheal tube. During the inspiration cycle, in which the respriator supplies air to the patient's lungs, the diaphragm is displaced and inflates the endotracheal tube cuff into sealing engagement with the trachea. On expiration cycles, in which air is exhausted from the lungs, the diaphragm returns to its normal position, causing at least partial deflation of the inflatable cuff. This allows at least a portion of the air being exhausted from the lungs to pass around the endotracheal tube, allowing a tracheotomy patient to speak. The intermittent deflation of the cuff also reduces irritation of the tissue of the trachea.

5 Claims, 1 Drawing Sheet

ENDOTRACHEAL TUBE SEALING CUFF SYSTEM

BACKGROUND OF THE INVENTION

This invention relates generally to endotracheal tube systems, and more particularly to a novel and improved apparatus for controlling the inflation of the cuff of an endotracheal tube.

PRIOR ART

It is known to provide respirator systems which include endotracheal tubes providing a cuff which is inflated to provide a seal between the trachea and the tube so that air under pressure supplied by the respirator reaches the lungs. Such respirators operate through repeated cycles of alternate inspiration and expiration in which the lungs are first supplied with air under pressure during the inspiration cycle, followed by an expiration cycle in which the air is allowed to exhaust from the lungs.

Generally, in the past, the cuff has been continuously inflated so that both inspiration and expiration occurred solely through the endotracheal tube. This has produced a number of disadvantages. After a few days, the continuous pressure of the cuff on the trachea has led to sloughing of the bronchial mucosa, bronchial fistula, and eventually bronchial stenosis. Further, because all of the air is exhausted from the lungs through the endotracheal tube, the patient has been unable to speak.

In order to reduce the problem created by the continuous pressure of the cuff on the trachea, systems have been proposed which reduce the inflation pressure of the cuff during the expiration cycle of the system. Examples of such systems are illustrated in U.S. Pat. Nos. 4,119,101 and 4,501,273.

Further, s system has been described in U.S. Pat. No. 4,090,518, in which a cuff is directly connected to the breathing tube and is inflated and deflated in accordance with the fluctuating pressure therein. It is indicated in such patent that the system permits exhalation of air through the natural nasal passageway.

SUMMARY OF THE INVENTION

In accordance with the present invention, a novel and improved apparatus is provided in which a simple and reliable cuff inflation control system for the endotracheal cuff controls the inflation thereof so that the seal is maintained between the cuff and the trachea only during the inspiration cycle in which air is supplied from the respirator to the patient's lungs. During the expiration cycle, in which the air previously supplied to the lungs is exhausted, the endotracheal cuff is deflated a sufficient amount that at least a portion of the air previously supplied to the lungs escapes along the trachea around the cuff.

It has been found that with such apparatus the sloughing of the bronchial mucosa, bronchia fistula, and eventual bronchial stenosis are drastically reduced, or eliminated. Further, with such system, a tracheotomy patient can speak during the expiration cycle.

In the illustrated embodiment, a control is provided having a housing having a passage therethrough. One end of the passage is connected to the respirator, and the other end is connected to the endotracheal tube so that the pressure within the passage cycles between the output pressure of the respirator during the inspiration cycle and the exhaust pressure (usually atmospheric pressure) during the expiration cycle.

Connected to the passage is a diaphragm chamber, also defined by the housing. Such chamber is divided by a flexible diaphragm into first and second diaphragm chamber portions. The diaphragm functions to isolate the first chamber portion from the second chamber portion. The first chamber portion is connected to the housing passage. The second chamber is connected to the endotracheal tube cuff and forms therewith a closed system which is physically isolated from the interior of the endotracheal tube and the respirator, but is in fluid pressure communication therewith through the flexible diaphragm.

The closed system, including the second chamber portion and the cuff, is supplied with sufficient gas, usually air, to ensure that the cuff provides a seal with the trachea only during the inspiration cycle and deflates a sufficient amount to allow at least a portion of the air exhausted from the lungs to pass around the cuff during the expiration cycle.

In the illustrated embodiment, the diaphragm is movable in response to differential pressure across the diaphragm between two maximum or limit positions. Further, the diaphragm is constructed and mounted so that it moves to and maintains one limit position when pressure in the first chamber portion does not exceed the pressure in the second chamber portion. This is the position the diaphragm assumes under the expiration cycle of operation.

During the inspiration cycle, the diaphragm moves from such one limit position and correspondingly increases the inflation pressure of the cuff. The displacement volume created by the movement of the diaphragm from its expiration position toward its maximum displaced position during inspiration is selected with respect to the volume of the cuff so that excessive pressure cannot be developed in the cuff during the inspiration cycle, but sufficient cuff inflation pressure is provided to establish a seal with the trachea so that the air from the respirator is delivered to the lungs.

Further, the control is structured so that the inflation pressure of the cuff during inspiration is slightly greater than the pressure of the air delivered by the endotracheal tube. This ensures that the cuff provides an effective seal.

With this invention, the irritation to the trachea and attendant problems discussed above are minimized, and a tracheotomy patient can speak during the expiration cycle of the respirator. Further, a simple, reliable structure is provided which is low in cost.

These and other aspects of this invention are illustrated in the accompanying drawings and are more fully described in the following specification.

DETAILED DESCRIPTION OF THE DRAWINGS

Figure 1:
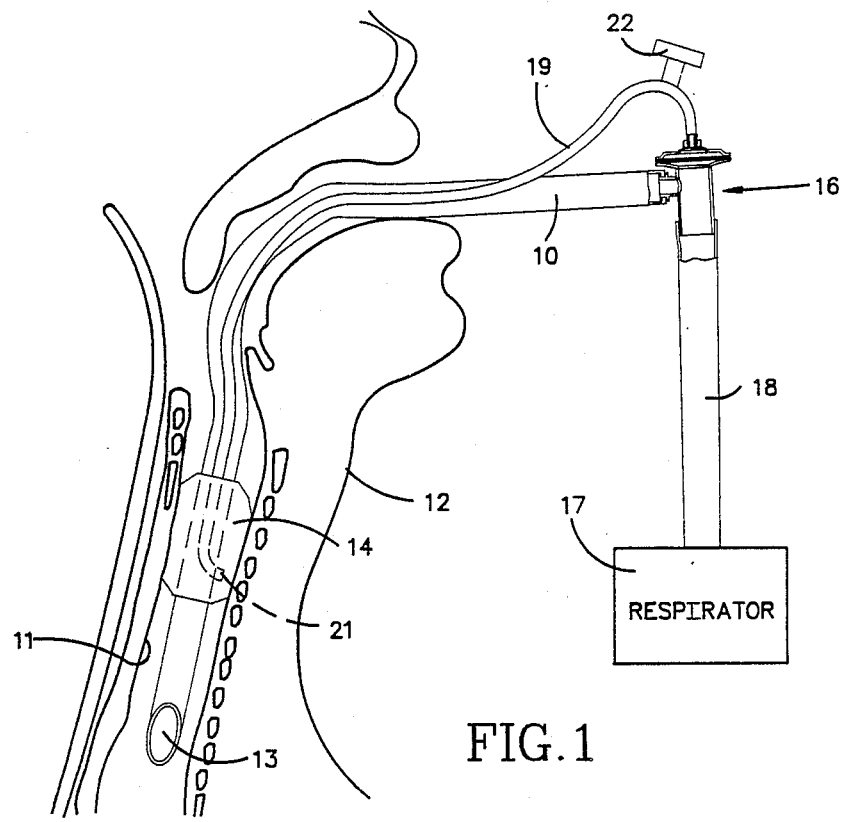
FIG. 1 is a schematic illustration of the overall system in accordance with this invention, incorporating the cuff inflation control.

FIG. 1 schematically illustrates the overall system in accordance with the present invention. Endotracheal tube 10 is positioned within the trachea 11 of a patient 12. Mounted on the tube 10 substantially adjacent to the inner end 13 thereof is an inflatable cuff 14 which, when inflated, forms a seal with the trachea 11. The other end of the endotracheal tube 10 is connected to an inflation control 16 in accordance with this invention.

The inflation control 16 is in turn connected to a respirator, schematically illustrated at 17, by a tube 18. The control 16 is also connected by a separate tube 19 to the interior of the cuff 14. Usually, the tube 14 extends along the interior of the endotracheal tube 10 so that only a single tube must be inserted into the patient's trachea. However, the interior of the tube 19 is isolated from the remaining interior of the endotracheal tube 10 and is connected at its inner end 21 to the inflatable cuff 14 and, as discussed in detail below, controls the inflation thereof. The inflation control tube 19 is provided with a self-sealing puncture plug 22 so that a measured amount of gas can be introduced into the inflation control tube by means of a hypodermic needle. Such plug is self-sealing when the hypodermic needle is removed.

Typically, the respirator is operated through repeated cycles of inspiration and expiration. During the inspiration cycle, air, which may for example be enriched with oxygen and the like, is delivered through the tube 18, the inflation control 16, and the endotracheal tube 10 to the lungs of the patient 12.

During such inspiration cycle, the cuff 14 is inflated with sufficient pressure to seal with the trachea so that the air supplied by the respirator 17 does not leak back out of the patient's mouth or nasal passages, but instead is forced by the pressure produced by the respirator 17 into the patient's lungs.

During the subsequent expiration cycle, the respiration reduces the pressure in the tube 18, usually to atmospheric pressure, so that the air previously delivered to the patient's lungs can flow out along the endotracheal tube.

In accordance with this invention, during the expiration cycle, the pressure within the cuff 14 is reduced simultaneously with the reduction in pressure in the tube 18 so that at least some of the air from the lungs flows out along the trachea around the tube 10.

When the cuff 14 is inflated and deflated in this manner, the sloughing of the bronchial mucosa, bronchial fistula, and bronchial stenosis is virtually eliminated even when the endotracheal tube is used continuously for an extended period of time. It is believed that the elimination of these problems by cyclically inflating the cuff and then deflating it results from the ability of the blood to return to the tissue of the trachea during the periods of deflation. Further, by allowing at least some of the air from the lungs to be exhausted through the trachea, a tracheotomy patient is able to speak.

Figure 2:
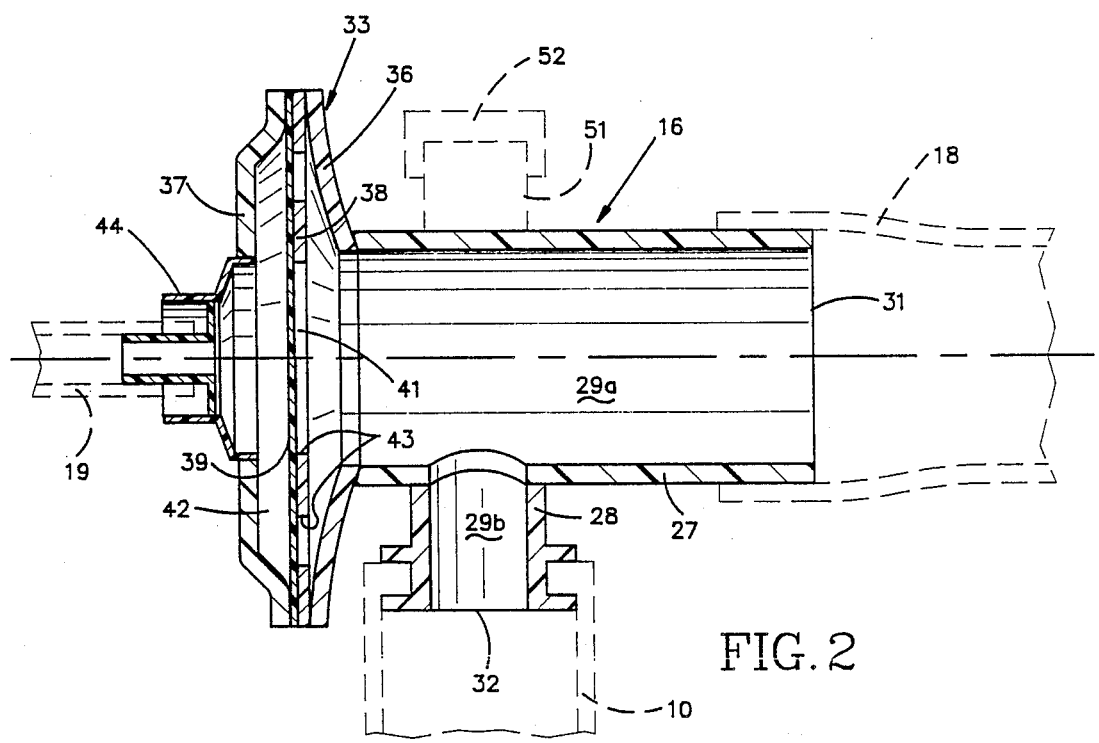
FIG. 2 is an enlarged, fragmentary view, in longitudinal section, illustrating one preferred embodiment of the control incorporating the present invention.

The inflation control 16 provides a housing 26 having a structure best illustrated in FIG. 2. The housing includes a pair of tubular elements 27 and 28 which are connected at right angles and cooperate to define a passage 29 through which the air is supplied to and exhausted from the endotracheal tube 10.

One end of the tube 27 is connected to the tube 18 and, in turn, is connected to the respirator 17. The other end of the passage 29 provided by the second tube 28 is directly connected to the endotracheal tube 10. Consequently, when air flows from the respirator through the tube 18, it enters the controls through a first end 31 of the passage 29 and then passes out of the second end 32 of the passage 29 into the endotracheal tube 10.

Conversely, during the expiration cycle, any air exhausted from a patient's lungs which passes through the endotracheal tube 10 enters the passage 29 through the ends 32 thereof and leaves the passage through the other end 31. As illustrated in FIG. 2 and as discussed in detail below, it is preferable to join the two tubes 27 and 28 so that the portion of the passage 29a within the tube 27 extends at right angles to the portion of the passage 29b, extending along the tube 28.

Mounted on the opposite end of the tubular element 27 is a diaphragm housing portion 33 consisting of housing parts 36 and 27 which cooperate to define a diaphragm chamber. The diaphragm housing portion 33 also includes a divider plate 38 and a flexible diaphragm 39 which function to divide the diaphragm chamber into a first chamber portion 41 and a second chamber portion 42. The housing part 36 is slightly concave and is secured to the adjacent end of the tube 26 with a fluidtight joint. The housing part 36 is also provided with a central aperture so that the first chamber portion 41 is in direct fluid communication with the passage 29a. The divider plate 38 is formed with a plurality of apertures 43 so that the adjacent side of the flexible diaphragm 39 is also in fluid communication with the first chamber portion 41.

The diaphragm 39, the divider plate 38, and the two housing parts 36 and 37 are joined at their peripheries so that they cooperate to define the two chamber portions 41 and 42, which are isolated from each other by the flexible diaphragm 39. The housing part 37 is also formed with a concave shape which determines the maximum volume of the chamber portion 42.

A fitting 44 is secured to the housing part 37 and, in turn, provides a connection for the tube 19.

Preferably, all of the various components of the inflation control 16, with the exception of the diaphragm 29, are formed of a clear plastic so that the condition within the control is externally visible. Further, the various components are connected together by suitable means, such as adhesive, heat or solvent welding, so that a permanent assembly is provided. The diaphragm 39 is preferably formed of very thin elastomeric material, and is movable between its normal condition of minimum stress against the divider plate 38, which constitutes one limit position, to the left as viewed in FIG. 2 when the pressure in the first chamber portion 41 exceeds the pressure in the second chamber portion 42.

In effect, two fluid circuits are provided which are isolated from each other but are interrelated in pressure by the diaphragm 39.

In use, the endotracheal tube is inserted into the patient's mouth and down along the trachea 11 until the cuff 14 is properly positioned within the trachea. During such insertion of the endotracheal tube, the cuff 14 is fully deflated by inserting a hypodermic needle into the puncture plug 22 and evacuating the gas from the cuff 14, the tube 19, and the chamber portion 42. After the cuff is properly positioned, air is introduced into the closed section of the system, again by the insertion of a hypodermic needle into the puncture plug 22. Sufficient air is introduced to cause partial inflation of the cuff. During such partial inflation of the cuff, the diaphragm 39 remains in the position of least stress illustrated in FIG. 2 against the divider plate 38.

The control is then connected to the respirator 17 through the tube 18 and the respirator is started. During the inspiration cycle in which air is supplied to the tube 18 under sufficient pressure to fill the lungs, the air flows in along the passage 29a and then laterally out through the passage 29b into the endotracheal tube. This pressure acts against the adjacent side of the diaphragm and displaces the diaphragm to the left as illustrated in FIG. 2, causing inflation of the cuff 14 a sufficient amount to produce a seal between the cuff 14 and the wall of the trachea 11. Therefore, the air cannot leak out through the patient's natural passages and must flow into the lungs.

On the expiration portion of the cycle, the pressure in the tube is reduced, in most cases, to atmospheric pressure, which reduces the pressure in the passages 29a and 29b. Since the differential pressure does not then exist across the diaphragm 39, the diaphragm returns to its normal position against the divider and partially deflates the cuff 14. This allows a portion of the air from the lungs to pass around the cuff and out through the patient's natural passages.

The flow path during inspiration along the passage 29a and out through the passage 29b is at right angles. Therefore, the pressure against the diaphragm exceeds the pressure within the passageway 29b by the amount of the impact pressure caused by the velocity of flow through the passageways 29a and 29b. Consequently, the pressure against the diaphragm always exceeds the pressure within the passageway 29b by a small amount during the inspiration cycle. This ensures that sufficient pressure exists within the cuff to ensure a good seal with the trachea.

The volume of the chamber portion 42,, however, is selected so that when the diaphragm moves to the left as viewed in FIG. 2 against the chamber part 37, excessive pressure cannot be developed. The volume of the chamber portion 42 with respect to the volume of the cuff 14 limits the maximum inflation pressure of the cuff 14. Therefore, if the patient coughs or otherwise creates a high pressure within the endotracheal tube, that pressure can only move the diaphragm to its other limit position determined by the housing part 37 and excessive pressure cannot be developed in the cuff.

If desired, an additional port, illustrated in phantom at 51, can be provided on the control to allow connection to a suction system. In normal operation, if such an additional port 51 is provided, such port is closed by a cap 52.

With the present invention, a very reliable, structurally simple control is provided which modulates the inflation pressure of the cuff 14 so that a satisfactory seal is provided during the inspiration cycle and which ensures that the cuff is deflated a sufficient amount during the expiration cycle to allow at least some of the air from the lung to pass around the endotracheal tube. This has been found to minimize or eliminate the sloughing of the bronchial mucosa, bronchial fistula, and eventual bronchial stenosis. Further, it allows a tracheotomy patient to speak during the expiration cycle.

Although the preferred embodiment of this invention has been shown and described, it should be understood that various modifications and rearrangements of the parts may be resorted to without departing from the scope of the invention as disclosed and claimed herein.

What is claimed is:

1. A pressure transfer device for controlling the inflation of the inflatable cuff for an endotracheal tube comprising a housing providing a passage and a chamber, said passage being connectible between the respirator and an endotracheal tube so that air supplied by said respirator to said endotracheal tube passes through said passage, a resilient diaphragm dividing said chamber into first and second chamber portions, said diaphragm isolating said first and second chamber portions and being movable between two limit positions in response to differential pressure between said first and second chamber portions, said first chamber portion being connected to said passage, said second chamber portion being adapted to be connected to said cuff and provide therewith a fluidtight system, said diaphragm being movable to one of said limit positions when said respirator supplies pressure to said first chamber portion and causing said cuff to inflate, said diaphragm being movable to the other of said limit positions when said respirator is exhausting and causing said cuff to be at least partially deflated; said housing being shaped so that said passage provides a first portion having an end for connection to a respirator and a second portion extending at an angle from said first portion and providing an end for connection to said endotracheal tube, said first chamber portion being connected to said first passage portion at a location on the side of said first passage portion remote from said end of said first passage portion and in alignment therewith, air entering said first passage portion and subsequently passing through said second passage portion being turned through said angle causing the pressure in said first chamber portion to exceed the pressure in said second passage portion when air is supplied to said passage by said respirator, the passage being free of structure substantially restricting air flow therethrough.

2. A pressure transfer device as set forth in claim 1, wherein said second chamber portion and said diaphragm are sized so that the volume displaced by movement of said diaphragm between said two limit positions is insufficient to produce excessive inflation of said cuff.

3. A pressure transfer device for controlling the inflation and deflation of an inflatable cuff of an endotracheal tube comprising a housing providing:
    (a) a first substantially straight passage portion having first and second ends;
    (b) a second passage portion having first and second ends, said first end of said second passage portion being connected to said first passage portion intermediate the ends of said first passage portion and extending at an angle therefrom;
    (c) a diaphragm chamber divided into first and second chamber portions by an elastic diaphragm, said first chamber portion being connected to said second end of said first passage portion;
    (d) said first end of said first passage portion being connectible to a respirator, said second end of said second passage portion being connectible to an endotracheal tube, said second chamber portion being connectible to said inflatable cuff;
    air entering said first passage portion and subsequently passing through said second passage portion being turned through said angle causing the pressure in said first chamber portion to exceed the pressure in said second passage portion when said respirator is supplying air to said endotracheal tube;
    the passage being free of structure which substantially restricts flow of air therethrough.

4. A pressure transfer device as set forth in claim 3, wherein said housing provides a first substantially straight tube element defining said first passage portion, a second tube element extending substantially at right angles from said first tube element defining said second passage portion, and a pair of chamber parts defining said diaphragm chamber, one of said chamber parts being mounted on the end of said first tube element and being open thereto, said diaphragm being mounted at its periphery between said first and second chamber parts.

5. A pressure transfer device as set forth in claim 4, in combination with a respirator connected to said end of said first passage, an endotracheal tube connected to said second end of said second passage portion and an inflatable cuff mounted on said endotracheal tube, said cuff being connected to said second chamber portion and isolated from said passage by said diaphragm, pressure in said passage created by said respirator and causing flow of air from said respirator to said endotracheal tube causing displacement of said diaphragm to inflate said cuff, said diaphragm returning from its displaced position and allowing partial deflation of said cuff when said respirator connects said passage to atmospheric pressure.

* * * * *